(12) United States Patent
Harada et al.

(10) Patent No.: US 12,059,471 B2
(45) Date of Patent: Aug. 13, 2024

(54) COMPLEX

(71) Applicants: UNITED IMMUNITY, CO., LTD., Mie (JP); KYOTO UNIVERSITY, Kyoto (JP)

(72) Inventors: Naozumi Harada, Mie (JP); Kazunari Akiyoshi, Kyoto (JP); Shin-ichi Sawada, Kyoto (JP)

(73) Assignees: UNITED IMMUNITY, CO., LTD., Mie (JP); KYOTO UNIVERSITY, Kyoto (JP)

( * ) Notice: Subject to any disclaimer, the term of this patent is extended or adjusted under 35 U.S.C. 154(b) by 44 days.

(21) Appl. No.: 17/470,643

(22) Filed: Sep. 9, 2021

(65) Prior Publication Data
US 2022/0111061 A1 Apr. 14, 2022

Related U.S. Application Data

(63) Continuation of application No. PCT/JP2020/034346, filed on Sep. 10, 2020.

(51) Int. Cl.
*A61K 47/61* (2017.01)
*A61K 47/54* (2017.01)
*A61K 47/55* (2017.01)

(52) U.S. Cl.
CPC ............ *A61K 47/61* (2017.08); *A61K 47/549* (2017.08); *A61K 47/55* (2017.08); *A61K 47/554* (2017.08)

(58) Field of Classification Search
CPC .................. C12N 15/117; A61K 2039/55561
See application file for complete search history.

(56) References Cited

U.S. PATENT DOCUMENTS

| 2014/0079738 A1 | 3/2014 | Nishikawa et al. |
| 2014/0322344 A1 | 10/2014 | Shiku et al. |
| 2019/0343946 A1 | 11/2019 | Cooper et al. |

FOREIGN PATENT DOCUMENTS

| JP | 2018-516847 | 6/2018 |
| JP | 2018-115159 | 7/2018 |
| KR | 10-2012-0001214 | 1/2012 |
| WO | 2012/144560 | 10/2012 |
| WO | 2013/031882 | 3/2013 |
| WO | 2016/154544 | 9/2016 |

OTHER PUBLICATIONS

Tahara et al. "Current advances in self-assembled nanogel delivery systems for immunotherapy", Advanced Drug Delivery Reviews 95 (2015) 65-76 (Year: 2005).*
Sasaki et al., "Nano-Bioengineering Using Nanogel as a Base Material", Recent Progress in Artificial Organs, 2010, vol. 39, No. 3, pp. 197-201, with partial English translation.
Muraoka et al., "Nanogel-Based Immunologically Stealth Vaccine Targets Macrophages in the Medulla of Lymph Node and Induces Potent Antitumor Immunity", ACS Nano, 2014, vol. 8, No. 9, pp. 9209-9218.
Muraoka et al., "Antigen delivery targeted to tumor-associated macrophages overcomes tumor immune resistance", J Clin Invest., 2019. vol. 129, No. 3, pp. 1278-1294.
Aso et al., "Design and Function of Adjuvants-Conjugated Nanogel", Proceedings of the Society of Polymer Science, Sep. 11, 2019, vol. 68, No. 2, with English translation.
The 68th Polymer debate, 28 pages, presented by inventors at University of Fukui, Sep. 25, 2019, relates to CD & CF.
Aso et al., "Design of Adjuvant-Loaded Nanogels for Immune Stimulation", Proceedings of the Society of Polymer Science, May 12, 2020, vol. 69, No. 1, with English translation.

* cited by examiner

*Primary Examiner* — James W Rogers
(74) *Attorney, Agent, or Firm* — Wenderoth, Lind & Ponack, L.L.P.

(57) ABSTRACT

An object is to provide a technique of forming CpG oligonucleotides and hydrophobized polysaccharides into complexes. This object is achieved by a complex comprising a modified CpG oligonucleotide containing a hydrophobic group A having a sterol skeleton, and a modified polysaccharide containing a hydrophobic group B.

10 Claims, 7 Drawing Sheets

Specification includes a Sequence Listing.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: K3 CpG ODN

<400> SEQUENCE: 1
atcgactctc gagcgttctc                                       20

<210> SEQ ID NO 2
<211> LENGTH: 20
<212> TYPE: DNA
<213> ORGANISM: Artificial Sequence
<220> FEATURE:
<223> OTHER INFORMATION: D35 CpG ODN

<400> SEQUENCE: 2
ggtgcatcga tgcagggggg                                       20

COMPLEX

TECHNICAL FIELD

The present invention relates to, for example, a complex comprising a modified polysaccharide.

BACKGROUND ART

The importance of immune cells, particularly macrophages (tumor-associated macrophages, abbreviated as "TAMs"), in cancer tissues has been pointed out as a factor influencing the malignancy of cancer. TAMs are known to be immunostimulatory (M1) and immunosuppressive (M2). M2 TAMs promote the malignant transformation and growth of cancer by reducing the immune attack against cancer. If immunosuppressive M2 TAMs can be converted to immunostimulatory M1 TAMs, the immune attack against cancer can be enhanced, and the malignant transformation and growth of cancer can be inhibited.

CpG oligonucleotides are able to stimulate innate immune receptors and thereby convert M2 TAMs to M1 TAMs. It is also possible to increase sensitivity to other immunotherapies (e.g., immune checkpoint inhibitors). However, CpG oligonucleotides have problems with systemic administration (e.g., intravenous administration) in terms of pharmacokinetics and safety.

It has been reported that since hydrophobized polysaccharides, such as cholesteryl pullulan, can be self-assembled to form nanogels, are highly biocompatible, function as protein carriers, and have the ability to suppress the degradation and aggregation of contained proteins, they are formed into complexes with proteins for use as antigen carriers (NPL 1). Further, it has been found that cholesteryl pullulan is accumulated in an intratumoral TAM selective manner (NFL 2), and is useful as a TAM selective delivery system.

CITATION LIST

Patent Literature

NPL 1: Muraoka, D. et al., ACS Nano, 8 (9), 9209-9218, 2014
NPL 2: Muraoka D. et al., J Clin Invest. 129(3): 1278-1294, 2019

SUMMARY OF INVENTION

Technical Problem

In the course of research, the present inventor focused on the formation of hydrophobized polysaccharides and CpG oligonucleotides into complexes. This can be expected to impart the above advantages of hydrophobized polysaccharides to CpG oligonucleotides, and to compensate for the above problems of CpG oligonucleotides. However, CpG oligonucleotides and hydrophobized polysaccharides cannot be directly formed into complexes.

An object of the present invention is to provide a technique of forming CpG oligonucleotides and hydrophobized polysaccharides into complexes.

Solution to Problem

When it is difficult to form hydrophobized polysaccharides and other substances into complexes, an attempt is generally made to form complexes after altering or modifying the hydrophobized polysaccharides, which are delivery carriers. As a result of intensive research in view of the above issues with such a background, the present inventor focused on the alteration or modification of CpG oligonucleotides. As a result of further research, the present inventor found that a complex comprising a modified CpG oligonucleotide containing a hydrophobic group A having a sterol skeleton, and a modified polysaccharide containing a hydrophobic group B can solve the above problem. As a result of still further research based on this finding, the present inventor has completed the present invention. Specifically, the present invention includes the following aspects.

Item 1. A complex comprising a modified CpG oligonucleotide containing a hydrophobic group A having a sterol skeleton, and a modified polysaccharide containing a hydrophobic group B.

Item 2. The complex according to Item 1, wherein a CpG oligonucleotide that forms the modified CpG oligonucleotide comprises at least one member selected from the group consisting of class A CpG oligonucleotides and class B CpG oligonucleotides.

Item 3. The complex according to Item 1 or 2, wherein the hydrophobic group A comprises at least one member selected from the group consisting of cholesterol-derived groups, cholestanol-derived groups, lanosterol-derived groups, ergosterol-derived groups, β-sitosterol-derived groups, campesterol-derived groups, stigmasterol-derived groups, and brassicasterol-derived groups.

Item 4. The complex according to any one of Items 1 to 3, wherein the number of nucleotides that form the modified CpG oligonucleotide is 8 to 50.

Item 5. The complex according to any one of Items 1 to 4, wherein a polysaccharide that forms the modified polysaccharide comprises at least one member selected from the group consisting of pullulan, dextran, amylose, amylopectin, and mannan.

Item 6. The complex according to any one of Items 1 to 5, wherein the polysaccharide that forms the modified polysaccharide comprises pullulan.

Item 7. The complex according to any one of Items 1 to 6, wherein the hydrophobic group B comprises a hydrophobic group having a sterol skeleton.

Item 8. The complex according to any one of Items 1 to 7, wherein the modified polysaccharide has a weight average molecular weight of 5000 to 2,000,000.

Item 9. The complex according to any one of Items 1 to 8, which contains 0.1 to 10 molar parts of the modified polysaccharide per molar part of the modified CpG oligonucleotide.

Item 10. The complex according to any one of Items 1 to 9, which is nanogel particles.

Item 11. A reagent comprising the complex according to any one of Items 1 to 10.

Item 12. A drug comprising the complex according to any one of Items 1 to 10.

Item 13. The drug according to Item 12, which is an immunomodulator, an anticancer agent, an adjuvant, or an antiviral agent.

Advantageous Effects of Invention

The present invention can provide a technique of forming CpG oligonucleotides and hydrophobized polysaccharides into complexes.

DESCRIPTION OF EMBODIMENTS

Figure 1:
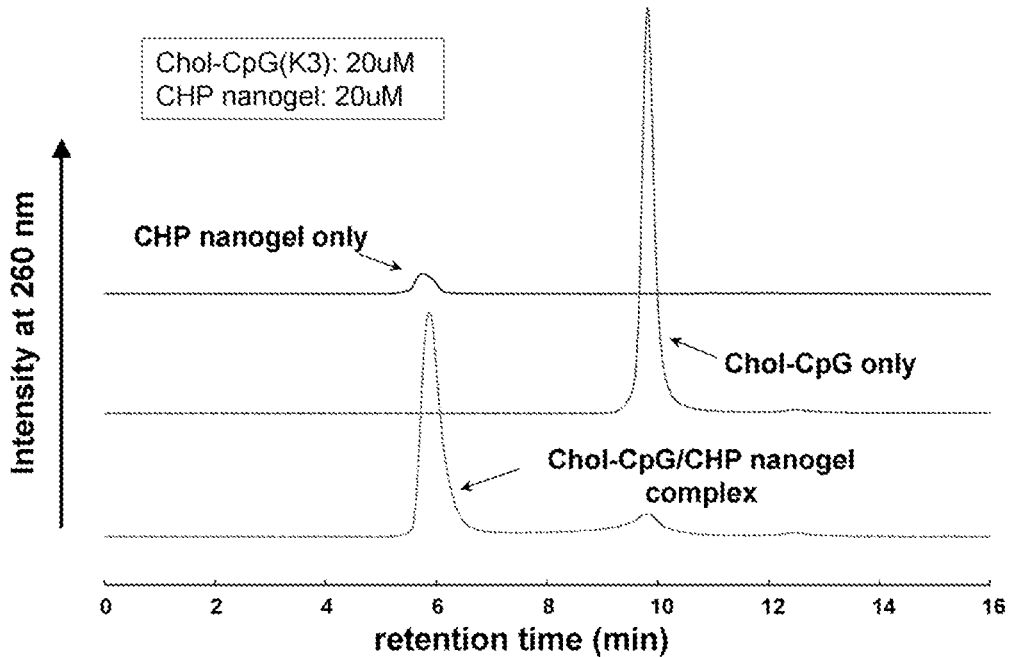
FIG. 1 shows the chromatograms of HPLC analysis results in the case of Chol-CpG (K3): 20 uM and CHP nanogel: 20 uM in Test Example 1-6.

In the present specification, the terms "comprise" and "contain" include the concepts of "comprise," "contain," "essentially consist of," and "consist of."

1. Complex

In an embodiment, the present invention relates to a complex comprising a modified CpG oligonucleotide containing a hydrophobic group A having a sterol skeleton, and a modified polysaccharide containing a hydrophobic group B (in the present specification, also referred to as "the complex of the present invention"). This is described below.

The modified CpG oligonucleotide is a compound obtained by modifying a CpG oligonucleotide, and is not particularly limited as long as it contains a hydrophobic group A having a sterol skeleton as a modifying group.

The CpG oligonucleotide that forms the modified CpG oligonucleotide (i.e., CpG oligonucleotide before modification) is not particularly limited as long as it is a single-stranded oligonucleotide containing an unmethylated cytosine-guanine dinucleotide (5'-CpG-3') motif (CpG motif). CpG oligonucleotides are known to be usable as vaccine adjuvants because they induce acquired immune responses via Toll-like receptors (TLRs). The CpG oligonucleotide may contain at least one CpG motif, or may contain multiple CpG motifs.

The number of nucleotides that form the CpG oligonucleotide is not particularly limited, but is, for example, 8 to 50 bases, preferably 8 to 40 bases, more preferably 8 to 30 bases, even more preferably 10 to 25 bases, still even more preferably 15 to 25 bases, and particularly preferably 18 bases to 25 bases.

CpG oligonucleotides are classified as class A (D-type), class B (K-type), class C, class P, and class S, based on the sequence, secondary structure, effects on human peripheral blood mononuclear cells (PBMCs), and the like. Preferable as CpG oligonucleotides among these are class A CpG oligonucleotides, class B CpG oligonucleotides, etc.

The internucleotide linkages in the CpG oligonucleotide can be phosphodiester linkages or phosphorothioate linkages. Phosphorothioate linkages can improve nuclease resistance. Class B CpG oligonucleotides generally have a linear structure with a phosphorothioate skeleton, and typically do not form a higher-order structure. Class A CpG oligonucleotides generally have a phosphodiester linkage in the center, and the poly-G motifs at both ends form a higher-order structure called a "G-tetrad."

Specific examples of CpG oligonucleotides are as follows.

Class A: D35-CpG, ODN1585, ODN2216, ODN2336, etc.
Class B: K3-CpG, ODNBW006, ODN D-SL01, ODN1668, ODN1826, ODN2006 (CpG7909, PF-3512676), ODN2007, ODN684, etc.
Class C: ODN D-SL03, ODN 2395, ODN M362, etc.

Other examples include CpG-28, CpG-685 (GNKG-168), ODN 0274, KSK-13 (KSK-CpG), CpG ODN 10104 (CpG-10104), CpG ODN-1585, ODN-5890, 1018-ISS, EMD-1201081 (HYB-2055, IMO-2055), and the like.

The CpG oligonucleotide used can be a commercially available product or a product obtained according to a known production method.

The hydrophobic group A is a hydrophobic group having a sterol skeleton, and is not particularly limited in that respect. The sterol skeleton is an alcohol in which a hydroxy group is attached to a cyclopentahydrophenanthrene ring shown in formula I. Symbols A to D in formula I represent each ring that forms the cyclopentahydrophenanthrene ring.

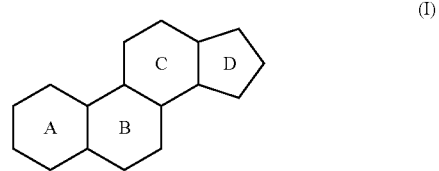

(I)

In the sterol skeleton, the cyclopentahydrophenanthrene ring may have a double bond, and the bonding position of the hydroxyl group is not limited. Preferable are either sterols with a hydroxy group at the C-3 position and a double bond in the B ring, or stanols with a hydroxy group at the C-3 position and a saturated ring. Examples of the hydrophobic group A include groups derived from compounds with a modified sterol skeleton, for example, the ring-forming carbon is replaced by a hydrocarbon group (e.g., a $C_{1-20}$ linear or branched alkyl group). The phrase "group derived from" refers to a group of a compound from which a hydrogen atom or a functional group, such as a hydroxyl group, is removed.

Examples of the hydrophobic group A include cholesterol-derived groups, cholestanol-derived groups, lanosterol-derived groups, ergosterol-derived groups, β-sitosterol-derived groups, campesterol-derived groups, stigmasterol-derived groups, brassicasterol-derived groups, and the like. Preferred among these are sterol-derived groups, such as cholesterol-derived groups, cholestanol-derived groups, lanosterol-derived groups, and ergosterol-derived groups; and more preferred are cholesterol-derived groups.

The number of nucleotides that form the modified CpG oligonucleotide is not particularly limited, but is, for example, 8 to 50 bases, preferably 8 to 40 bases, more preferably 8 to 30 bases, even more preferably 10 to 25 bases, still even more preferably 15 to 25 bases, and particularly preferably 18 bases to 25 bases.

The number of hydrophobic groups A contained in the modified CpG oligonucleotide is not particularly limited, and is 1 to 8, for example. This number is preferably 1 to 5, more preferably 1 to 3, even more preferably 1 or 2, and still even more preferably 1. Further, the number of hydrophobic groups A per 20 nucleotides that form the modified CpG oligonucleotide is preferably 1 to 8, more preferably 1 to 5, even more preferably 1 to 3, still even more preferably 1 or 2, and particularly preferably 1.

The linkage position of the hydrophobic group A in the modified CpG oligonucleotide is not particularly limited, and can be a terminal portion (5'-end or 3'-end) or a non-terminal portion (e.g., on a base). The linkage position is preferably a terminal portion.

The hydrophobic group A can be linked to the CpG oligonucleotide directly or indirectly (e.g., through a linker). The linker is not particularly limited, and examples include linkers in which several ethylene glycols are linked together (e.g., TEG linker and PEG linker), alkyl linkers, dSpacer, alkynyl dSpacer, dipropyl disulfide TEG linkers, and the like. When a linker is present, the number of atoms (e.g., carbon, oxygen, nitrogen, and sulfur atoms) forming the main chain of the linker is not particularly limited, but is, for example, 1 to 30, preferably 2 to 24, more preferably 4 to 18, and even more preferably 8 to 15.

The modified CpG oligonucleotide can be synthesized by or according to a known method for modifying oligonucleotides.

The modified CpG oligonucleotides can be used singly or in combination of two or more.

The modified polysaccharide is a compound obtained by modifying a polysaccharide, and is not particularly limited as long as it contains a hydrophobic group B as a modifying group.

The polysaccharide that forms the modified polysaccharide (i.e., polysaccharide before modification) is not particularly limited as long as it is a polymer to which a sugar residue is glycosidically linked. Usable examples of sugar residues that form the polysaccharide include residues derived from sugars, such as monosaccharides (e.g., glucose, mannose, galactose, and fucose), disaccharides, or oligosaccharides. The sugar residue may be 1,2-, 1,3-, 1,4-, or 1,6-glycosidically linked, and the linkage thereof may be either an α- or β-linkage. Further, the polysaccharide may be liner or branched. Preferable sugar residues are glucose residues. Preferable polysaccharides are, for example, naturally occurring or synthetic pullulan, dextran, amylose, amylopectin, mannan, and the like; preferably pullulan, mannan, and the like; and more preferably pullulan and the like.

The weight average molecular weight of the polysaccharide is not particularly limited as long as the modified polysaccharide can form nanogels, but is 5,000 to 2,000,000, for example. The weight average molecular weight of the polysaccharide is preferably 10,000 to 1,000,000, more preferably 20,000 to 500,000, even more preferably 40,000 to 250,000, and still even more preferably 80,000 to 125,000.

The polysaccharide used can be a commercially available product or a product obtained according to a known production method.

The hydrophobic group B is a group with hydrophobicity, and is not particularly limited as long as the modified polysaccharide can form, nanogels. For example, the hydrophobic group B is preferably a hydrophobic group having a sterol skeleton, a hydrocarbon group, or the like; and particularly preferably a hydrophobic group having a sterol skeleton.

The explanation of the hydrophobic group having a sterol skeleton is the same as that of the hydrophobic group A. Examples of the hydrocarbon group include, but are not particularly limited to, $C_{8-50}$ (preferably $C_{10-30}$, more preferably $C_{12-20}$) chain (preferably linear) hydrocarbon groups (preferably alkyl groups).

The weight average molecular weight of the modified polysaccharide is not particularly limited as long as the modified polysaccharide can form nanogels, but is 5,000 to 2,000,000, for example. The weight average molecular weight of the modified polysaccharide is preferably 10,000 to 1,000,000, more preferably 20,000 to 500,000, even more preferably 40,000 to 250,000, and still even more preferably 80,000 to 125,000.

The number of hydrophobic groups B contained in the modified polysaccharide is not particularly limited as long as the modified polysaccharide can form nanogels, but is, for example, 1 to 10, and preferably 1 to 5, per 100 sugar residues that form the polysaccharide.

The hydrophobic group B can be linked to the polysaccharide directly or indirectly (e.g., through a linker).

The modified polysaccharide is preferably, for example, one containing 1 to 10 (preferably 1 to 5) sugar units per 100 sugar residues that form the polysaccharide, whose primary hydroxyl group is represented by formula II: —O—$(CH_2)_n$CONH$(CH_2)_n$NH—CO—O—R (II), wherein R is a hydrophobic group having a sterol skeleton or a hydrocarbon group, m is 0 or 1, and n is any positive integer. n is preferably 1 to 8.

The modified polysaccharide can be synthesized by or according to a known method (e.g., WO00/12564). For example, the following method can be used. First, $C_{12-50}$ hydroxyl group-containing hydrocarbon or sterol, and a diisocyanate compound represented by formula OCN—$R^1$NCO, wherein $R^1$ is $C_{1-50}$ hydrocarbon group, are reacted to produce an isocyanato group-containing hydrophobic compound in which one molecule of $C_{12-50}$ hydroxyl group-containing hydrocarbon or sterol is reacted. Then, the resulting isocyanato group-containing hydrophobic compound and a polysaccharide are further reacted to produce a hydrophobic group-containing polysaccharide containing a $C_{12-50}$ hydrocarbon group or a steryl group as a hydrophobic group. The obtained reaction product is purified with a ketone solvent, whereby a high-purity hydrophobic group-containing polysaccharide can be produced.

The modified polysaccharides can be used singly or in combination of two or more.

The ratio of the modified CpG oligonucleotide and the modified polysaccharide in the complex of the present invention is not particularly limited. The complex of the present invention contains the modified polysaccharide in an amount of, for example, 0.1 to 10 molar parts, preferably 1 to 7 molar parts, and more preferably 2 to 4 molar parts, per molar part of the modified CpG oligonucleotide.

The complex of the present invention may be nanogel particles. The term "nanogel" refers to polymer gel nanoparticles with a hydrogel structure. The term "hydrogel" refers to a three-dimensional network structure formed by cross-linking of hydrophilic polymers and swelling with water. In the complex of the present invention as nanogel particles, the modified polysaccharide is self-assembled through physical crosslinks formed based on hydrophobic interactions with the hydrophobic group B, forming a three-dimensional network structure. When the complex of the present invention is nanogel particles, the modified CpG oligonucleotide is preferably present inside the nanogel particles.

The shape of the nanogel particles is not particularly limited, but is generally spherical.

The weight average particle diameter of the complex of the present invention is, for example, 100 nm or less, preferably 10 to 100 nm, more preferably 15 to 70 nm, and even more preferably 20 to 50 nm. The particle diameter can be measured by a dynamic light scattering method.

The complex of the present invention may contain substances other than the modified CpG oligonucleotide and the modified polysaccharide. Examples of other substances include proteins, peptides, nucleic acids, sugars, low-molecular-weight compounds, high-molecular-weight compounds, and minerals, as well as complexes thereof. The content of other substances is, for example, 0 to 10000 parts by mass, 0 to 1000 parts by mass, 0 to 500 parts by mass, 0 to 100 parts by mass, 0 to 50 parts by mass, or 0 to 10 parts by mass, based on 100 parts by mass of the total content of the modified CpG oligonucleotide and the modified polysaccharide.

The complex of the present invention can be produced by mixing a modified CpG oligonucleotide solution and a modified polysaccharide solution.

Each solution can be prepared by dissolving the modified CpG oligonucleotide or the modified polysaccharide in a solvent. As the solvent, for example, organic solvents, such as water and DMSO, can be used. The modified polysaccharide solution can be generally prepared by using water as the solvent. In this case, it is preferable to use a buffer solution, such as PBS, in place of water. The modified CpG oligonucleotide solution can be prepared by suitably selecting the solvent depending on the type thereof. For example, A-type CpG oligonucleotide can be generally prepared by using water as the solvent, and B-type CpG oligonucleotide can be generally prepared by using an organic solvent, such as DMSO, as the solvent.

The concentration of the modified CpG oligonucleotide in a mixed solution obtained by mixing the modified CpG oligonucleotide solution and the modified polysaccharide solution is not particularly limited, but is, for example, 1 to 50 uM, preferably 2 to 40 uM, more preferably 5 to 30 uM, and even more preferably 8 to 25 nM, from the viewpoint of the formation efficiency of nanogel particles.

The concentration of the modified polysaccharide in the mixed solution is not particularly limited, but is, for example, 5 to 100 uM, preferably 5 to 80 uM, and more preferably 8 to 50 uM, from the viewpoint of the formation efficiency of nanogel particles.

The molar ratio of the modified CpG oligonucleotide and the modified polysaccharide in the mixed solution is not particularly limited. From the viewpoint of the formation efficiency of nanogel particles, the amount of the modified polysaccharide is, for example, 0.1 to 4 mol, preferably 0.2 to 3 mol, more preferably 0.5 to 2.5 mol, and even more preferably 0.8 to 2.2 mol, per mol of the modified CpG oligonucleotide.

From the viewpoint of the formation efficiency of nanogel particles, it is preferable to subject the mixed solution to sonication, or to add a denaturant, such as urea, DMSO, or a surfactant, to the mixed solution and then remove the denaturant by dialysis. In terms of ease, the former method is more preferable. The latter method can be performed by or according to a known method.

Sonication can be performed, for example, by applying ultrasonic waves to a plastic tube containing the mixed solution and fixed on water in an ultrasonic bath tank. The sonication conditions are not particularly limited, but are, for example, 10 to 40° C. (preferably 20 to 35° C.), 10 to 50 kHz (preferably 20 to 40 kHz), 30 to 200 W (preferably 70 to 150 W), and 2 to 30 minutes (preferably 5 to 15 minutes). In an embodiment of the present invention, it is preferable to perform sonication first on the modified polysaccharide solution (e.g., 2 to 30 seconds, preferably 5 to 15 seconds), and after mixing with the modified CpG oligonucleotide, to further perform sonication (e.g., 2 to 30 minutes, preferably 5 to 15 minutes).

2. Use

The complex of the present invention contains a modified CpG oligonucleotide, and thus can exhibit the various effects of the CpG oligonucleotide (e.g., TLR stimulating action and various actions based thereon (e.g., inflammatory cytokine production promoting action, type I interferon production promoting action, etc.)). Therefore, the compound of the present invention can be used as an active ingredient of drugs, reagents, etc. (also referred to as "the drug of the present invention" in the present specification), specifically used for various uses based on TLR stimulation, and more specifically used as an active ingredient of, for example, immunomodulators, anticancer agents, antiviral agents, adjuvants (e.g., vaccine adjuvants), etc.

The drug of the present invention is not particularly limited as long as it comprises the complex of the present invention. The drug of the present invention may further contain other components, if necessary. The other components are not particularly limited as long as they are pharmaceutically acceptable components. Examples of the other components include additives in addition to components with pharmacological effects. Examples of additives include bases, carriers, solvents, dispersants, emulsifiers, buffers, stabilizers, excipients, binders, disintegrators, lubricants, thickeners, moisturizers, coloring agents, flavoring agents, chelating agents, and the like.

The usage mode of the drug of the present invention is not particularly limited, and a suitable usage mode can be used depending on the type thereof. The drug of the present invention can be used, for example, in vitro (e.g., added to a medium of cultured cells) or in vivo (e.g., administered to an animal) depending on the use thereof.

The application object of the drug of the present invention is not particularly limited. Examples of mammals include humans, monkeys, mice, rats, dogs, cats, rabbits, pigs, horses, cows, sheep, goats, deer, and the like. Further, examples of cells include animal cells and the like. The type of cell is also not particularly limited, and examples include blood cells, hematopoietic stem cells/progenitor cells, gametes (sperm and egg), fibroblasts, epithelial cells, vascular endothelial cells, neurons, hepatocytes, keratinocytes, muscle cells, epidermal cells, endocrine cells, ES cells, iPS cells, tissue stem cells, cancer cells, and the like.

When the drug of the present invention is used as an anticancer agent and used for cancer cells, the target cancer is not particularly limited. Examples include leukemia (including chronic lymphocytic leukemia and acute lymphocytic leukemia), lymphoma (including non-Hodgkin's lymphoma, Hodgkin's lymphoma, T-cell lymphoma, B-cell lymphoma, Berkit's lymphoma, malignant lymphoma, diffuse lymphoma, and follicular lymphoma), myeloma (including multiple myeloma), breast cancer, colon cancer, kidney cancer, gastric cancer, ovarian cancer, pancreatic cancer, cervical cancer, endometrial cancer, esophageal cancer, liver cancer, head and neck squamous epithelial cancer, skin cancer, malignant melanoma, urinary tract cancer, prostate cancer, villous cancer, pharyngeal cancer, laryngeal cancer, thecoma, male germinoma, endometrial hyperplasia, endometriosis, embryoma, fibrosarcoma, Kaposi sarcoma, hemangioma, cavernous hemangioma, hemangioblastoma, retinoblastoma, astrocytoma, neurofibroma, oligodendroglioma, medulloblastoma, neuroblastoma, glioma, rhabdomyosarcoma, medulloblastoma, osteogenic sarcoma, leiomyosarcoma, thyroid sarcoma, Wilms tumor, and the like.

The drug of the present invention can have any dosage form, and examples include oral dosage forms, such as tablets (including orally disintegrating tablets, chewable tablets, foaming tablets, troches, jelly drops, etc.), pills, granules, subtle granules, powders, hard capsules, soft capsules, dry syrups, liquids (including drinkable preparations, suspensions, and syrups), and jellies; and parenteral dosage forms, such as injectable preparations (e.g., drip injections (intravenous drip injections etc.), intravenous injections, intramuscular injections, subcutaneous injections, and intradermal injections), external preparations (e.g., ointments, poultices, and lotions), suppositories, inhalants, eye drops, eye ointments, nasal drops, ear drops, and liposome preparations.

The route of administration of the drug of the present invention is not particularly limited as long as desired effects are obtained. Examples include enteral administration, such as oral, tube feeding, and enema administration; parenteral administration, such as intravenous, intraarterial, intramuscular, intracardiac, subcutaneous, intradermal, and intraperitoneal administration; and the like.

The content of the active ingredient in the drug of the present invention varies depending on the usage mode, application object, the state of the applied object, etc., and is not limited. For example, the content of the active ingredient is 0.0001 to 100 wt. %, and preferably 0.001 to 50 wt. %.

The dose of the drug of the present invention when administered to an animal is not particularly limited as long as it is an effective amount for expressing drug effects. In the case of oral administration, the weight of the active ingredient is generally 0.1 to 1000 mg/kg body weight per day, and preferably 0.5 to 500 mg/kg body weight per day. In the case of parenteral administration, the weight of the active ingredient is 0.01 to 100 mg/kg body weight per day, and preferably 0.05 to 50 mg/kg body weight per day. The above dose can be suitably increased or decreased according to the age, pathological conditions, symptoms, etc.

The drug of the present invention can be used in combination with other drugs. Examples of other drugs include anticancer agents.

Examples of anticancer agents include alkylating agents, antimetabolites, microtubule inhibitors, antibiotic anticancer agents, topoisomerase inhibitors, platinum preparations, molecular-targeted drugs, hormonal agents, biologics, and the like.

Examples of alkylating agents include cyclophosphamide, ifosfamide, nitrosourea, dacarbazine, temozolomide, nimustine, busulfan, melphalan, procarbazine, ranimustine, and the like.

Examples of antimetabolites include enocitabine, carmofur, capecitabine, tegafur, tegafur uracil, tegafur gimeracil oteracil potassium, gemcitabine, cytarabine, cytarabine ocfosfate, nelarabine, fluorouracil, fludarabine, pemetrexed, pentostatin, methotrexate, cladribine, doxifluridine, hydroxycarbamide, mercaptopurine, and the like.

Examples of microtubule inhibitors include alkaloid anticancer agents, such as vincristine; and taxane anticancer agents, such as docetaxel and paclitaxel.

Examples of antibiotic anticancer agents include mitomycin C, doxorubicin, epirubicin, daunorubicin, bleomycin, actinomycin D, aclarubicin, idarubicin, pirarubicin, peplomycin, mitoxantrone, amrubicin, zinostatin stimalamer, and the like.

Examples of topoisomerase inhibitors include CPT-11, irinotecan, and nogitecan, all of which have topoisomerase I inhibitory action; and etoposide and sobuzoxane, both of which have topoisomerase II inhibitory action.

Examples of platinum preparations include cisplatin, nedaplatin, oxaliplatin, carboplatin, and the like.

Examples of hormonal agents include dexamethasone, finasteride, tamoxifen, astrozole, exemestane, ethinyl estradiol, chlormadinone, goserelin, bicalutamide, flutamide, brednisolone, leuprorelin, letrozole, estramustine, toremifene, fosfestrol, mitotane, methyltestosterone, medroxyprogesterone, mepitiostane, and the like.

Examples of biologics include interferon-$\alpha$, -$\beta$, and -$\gamma$, interleukin-2, ubenimex, dried BCG, and the like.

Examples of molecular-targeted drugs include rituximab, alemtuzumab, trastuzumab, cetuximab, panitumumab, imatinib, dasatinib, nilotinib, gefitinib, erlotinib, temsirolimus, bevacizumab, VEGF trap, sunitinib, sorafenib, tocizumab, bortezomib, gemtuzumab ozogamicin, ibritumomab ozogamicin, ibritumomab tiuxetan, tamibarotene, tretinoin, and the like. In addition to the molecular-targeted drugs specified herein, other examples of molecular-targeted drugs include immune checkpoint inhibitors, such as anti-PD-1 antibodies (e.g., nivolumab and pembrolizumab), anti-PD-L1 antibodies (e.g., tecentrig, durvalumab, and avelumab), and anti-CTLA-4 antibodies (e.g., ipilimumab); inhibitors targeting angiogenesis, such as human epidermal growth factor receptor 2 inhibitors, epidermal growth factor receptor inhibitors, Bcr-Abl tyrosine kinase inhibitors, epidermal growth factor tyrosine kinase inhibitors, mTOR inhibitors, and vascular endothelial growth factor receptor 2 inhibitors ($\alpha$-VEGFR-2 antibody); various tyrosine kinase inhibitors, such as MAP kinase inhibitors; cytokine-targeted inhibitors, proteasome inhibitors, and antibody-anticancer agent formulations. These inhibitors also include antibodies.

The structure, dosage form, usage mode, etc. of the other drugs are the same as those of the drug of the present invention.

EXAMPLES

The present invention is described in detail below based on Examples; however, the present invention is not limited to these Examples.

Test Example 1. Complexation Test of CHP Nanogel and Chol-CpG (K3)

Test Example 1-1. Preparation of CHP

According to a previously reported document (Macromolecules 1993, 23, 3062-3068), cholesterol-modified pullulan (CHP) was produced by introducing 1.2 cholesterols per 100 monosaccharides to pullulan having a weight average molecular weight of 450,000.

Test Example 1-2. Preparation of Chol-CpG (K3)

Cholesterol-modified K3 CpG (Choi-CpG (K3)), in which cholesterol was linked to the 5'-end of K3 CpG oligonucleotide (SEQ ID NO 1: 5'-atcgactctcgagcgttctc, linkages between all nucleotides are phosphorothioate linkages) through a triethylene glycol linker, was custom-synthesized by Gene Design Inc.

Test Example 1-3. Preparation of CHP Nanogel Solution

CHP was added to PBS to 0 to 20 UM, and dissolved by stirring with a stirrer at 25° C. for 15 hours. Then, ultrasonic waves were intermittently applied for 6 minutes using a probe type ultrasonic wave generating device. After this solution was centrifuged at 25° C. and 20000 g for 30 minutes, the supernatant was sterilized by filtration through a 0.22-um filter. In the Examples, CHP solutions were prepared in this manner, regardless of the type of solvent. The weight average molecular weight of CHP nanogel was 450,000 in terms of molar concentration.

Test Example 1-4. Preparation of Chol-CpG (K3) Solution

DMSO was added to the custom-synthesized Chol-CpG (K3) to 400 uM, and dissolved by stirring.

Test Example 1-5. Complexation of CHP Nanogel and Chol-CpG (K3)

The CHP nanogel solution (Test Example 1-3) was diluted with PBS to a concentration of 0-20 uM, and 76 uL of the CHP nanogel solution was placed in a plastic tube. The tube was fixed directly above an ultrasonic oscillator in an ultrasonic bath tank filled with water, and ultrasonic irradiation was started at a water temperature of 25 to 30° C., 28 kHz, 100 W. After 5 to 10 seconds, 400 uM of a Chol-CpG (K3)/DMSO solution (4.0 uL) was added to the CHP nanogel solution using a micropipette. After the addition, ultrasonic irradiation was continued for 10 minutes, and the obtained solution was used as a Chol-CpG (K3)/CHP nanogel complex sample for further analysis.

Test Example 1-6. HPLC Analysis of Complex

As complexation evaluation of the Chol-CpG (K3)/CHP nanogel complex sample prepared in Test Example 1-5, size exclusion chromatography (SEC) was carried out. The conditions were as follows. Column: G3000SWXL (Tosoh Corporation), 7.8 mm×150 mm, detector: UV (260 nm), column detection temperature: 35° C., injection amount: 20 uL, flow rate: 0.5 mL/min, eluent: PBS (pH: 7.4). Using PBS as an eluent, the eluate was detected at 260 nm, which was an absorption wavelength specific to CpG, which was a nucleic acid adjuvant.

The results (chromatograms) of Chol-CpG (K3): 20 uM and CHP nanogel: 20 uM are shown in FIG. 1. In the chromatogram of CHP nanogel (20 uM) alone (blue line), only a small peak due to light scattering of the nanogel was detected at around 6 minutes. Further, in the chromatogram, of Chol-CpG (K3) (20 uM) alone (red line), a large single peak derived from Chol-CpG (K3) was detected at around 10 minutes. On the other hand, in the chromatogram of the sample that was complexed under the condition in which the final concentration of CHP nanogel and Chol-CpG (K3) was 20 uM (green line), a large single peak was detected at around 6 minutes, which was the elution time of the nanogel, and only a small peak was observed at around 10 minutes, which was the elution time of Chol-CpG (K3). The appearance of a large single peak at around 6 minutes in the complex sample indicates that the nanogel and Chol-CpG (K3) formed a complex. This can also be confirmed by the significant decrease in the Chol-CpG (K3) single peak, which should have been detected at around 10 minutes.

Figure 2:
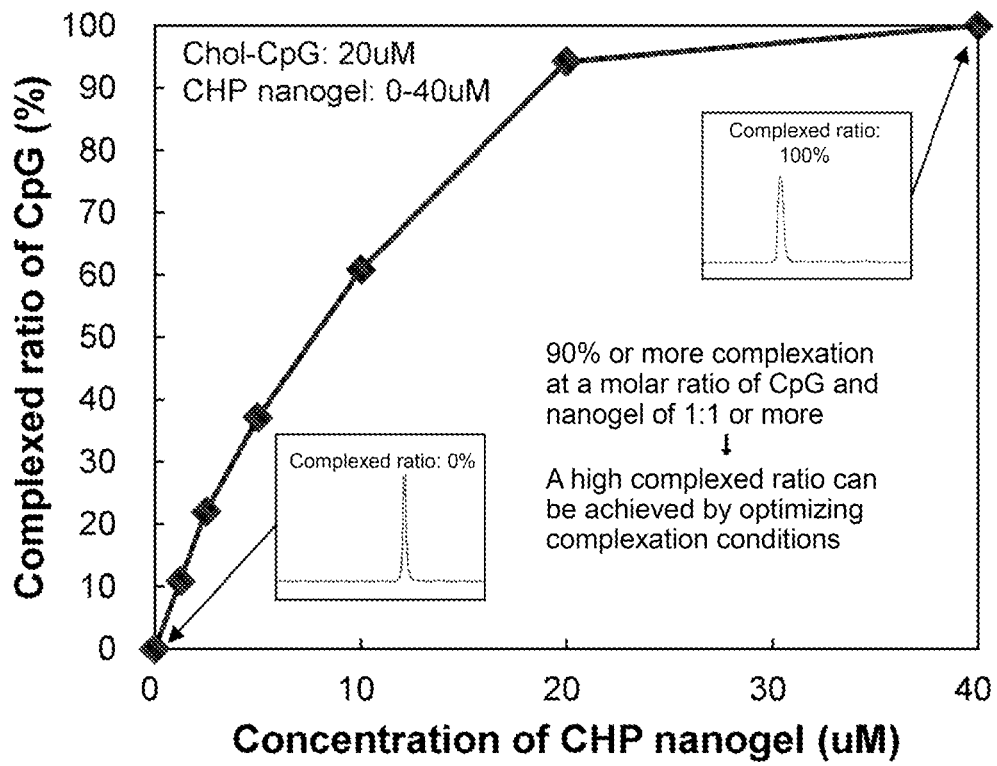
FIG. 2 shows the complexed ratio of the HPLC analysis results in Test Example 1-6 when changing the final concentration of CHP nanogel in the range of 0 to 40 uM while setting the final concentration of Chol-CpG (K3) to 20 uM.

FIG. 2 shows the results of changing the final concentration of CHP nanogel within the range of 0 to 40 uM while setting the final concentration of Chol-CpG (K3) to 20 uM (complexed ratio). The area of a peak derived from Chol-CpG (K3) that was not complexed with the nanogel at around 10 minutes was analyzed, and the complexed ratio with the nanogel was graphed. With the increase of the CHP nanogel concentration during complexation, the non-complexed Chol-CpG (K3)-derived peak decreased. The complexed ratio was almost 100% at a molar ratio of nanogel with a CHP nanogel concentration of 40 uM and Chol-CpG (K3) of 2:1, and the complexed ratio was about 95% at a molar ratio of 1:1.

Test Example 1-7. Evaluation of Physical Properties of Complex (DLS)

Figure 3:
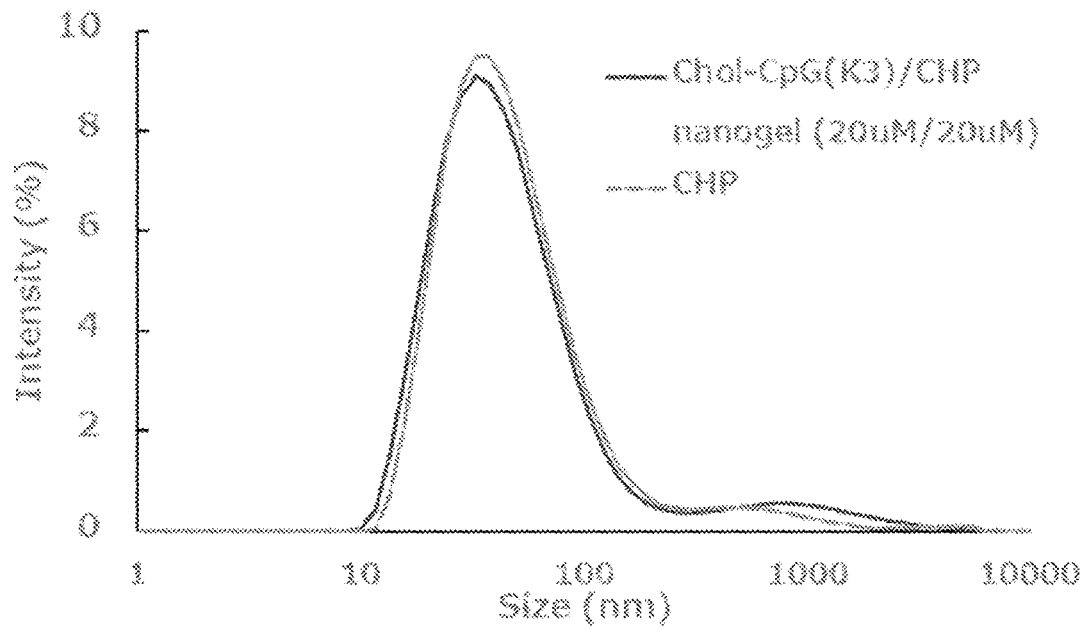
FIG. 3 shows the particle size distribution by DLS measurement in Test Example 1-7.

For the complex prepared in Test Example 1-5 with Chol-C G (K3): 20 uM and CHP nanogel: 20 uM, the average particle diameter obtained by cumulant analysis was measured using a dynamic light scattering (DLS) instrument. The complex sample and CHP nanogel alone (final concentration: 20 uM) were placed in a DLS measurement cell, and set in the DLS instrument (Zetasizer Nano ZS, produced by Malvern) for measurement. The results are shown in Table 1 and FIG. 3.

TABLE 1

|  | $D_H$ (nm) | PDI |
| --- | --- | --- |
| CHP | 32.6 ± 5.9 | 0.24 ± 0.02 |
| Chol-CpG(K3)/ CHP nanogel (20 uM/20 uM) | 39.2 ± 4.9 | 0.33 ± 0.04 |

The average particle diameter was about 33 nm in CHP nanogel alone (final concentration: 20 uM), and about 39 nm in the complex sample. The particle diameter of the complex sample was several nm larger than that of CHP nanogel alone; however, no significant increase in particle diameter due to aggregate formation was detected.

Test Example 1-8. Evaluation of Physical Properties of Complex (TEM)

The complex prepared in Test Example 1-5 with Chol-CpG (K3): 20 uM and CHP nanogel: 20 uM was observed with transmission electron microscopy (TEM). 10 uL of the complex sample was cast on an elastic carbon support film for TEM observation and allowed to stand for 10 minutes, and then the liquid was absorbed by filter paper. Next, 10 uL of a phosphotungstic acid aqueous solution was cast on the support film and allowed to stand for 1 minute to stain. Then, the staining solution was absorbed by filter paper, followed by drying under reduced pressure overnight, and TEM observation was performed.

Figure 4:
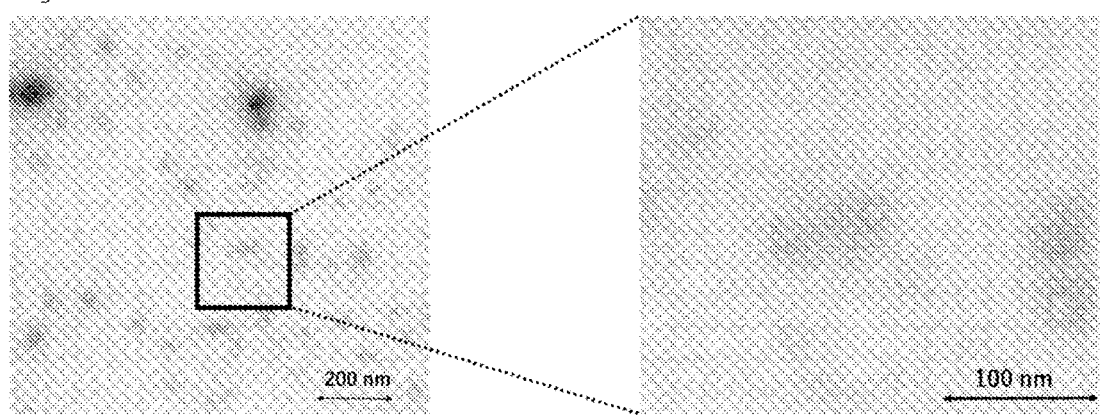
FIG. 4 shows TEM observation images in Test Example 1-8.

The results are shown in FIG. 4. As a result of TEM observation (lower part of slide 11), a circular structure of about 20 to 30 nm was observed. The TEM observation and the above DLS confirmed that the Chol-CpG (K3)/CHP nanogel complex obtained by complexation operation did not form aggregates, and maintained the same particle diameter as CHP nanogel alone.

Test Example 2. Complexation Test of CHP Nanogel and Chol-CpG (D35)

Test Example 2-1. Preparation of Chol-CpG (D35)

Cholesterol-modified D35 CpG (Chol-CpG (D35)), in which cholesterol was linked to the 5'-end of D35

CpG oligonucleotide (SEQ ID NO 2: 5'-g^gtgcatc-gatgcagggg^g^g; ^ represents a phosphorothioate linkage, and other linkages are phosphodiester linkages) through a triethylene glycol linker, was custom-synthesized by Gene Design Inc.

Test Example 2-2. Preparation of Chol-CpG (D35) Solution

Sterile distilled water was added to the custom-synthesized Chol-CpG (D35) to 200 uM, and dissolved by stirring, followed by heating at 90° C. for 5 minutes and cooling to room temperature.

Test Example 2-3. Complexation of CHP Nanogel and Chol-CpG (D35)

The CHP nanogel solution (Test Example 1-3) was diluted with sterile distilled water to a concentration of 0 to 20 mg/mL, and 72 uL of the CHP nanogel solution was placed in a plastic tube. The tube was fixed directly above an ultrasonic oscillator in an ultrasonic bath tank filled with water, and ultrasonic irradiation was started at 28 kHz, 100 W. After 5 to 10 seconds, 200 uM of a Chol-CpG (D35)/water solution (8.0 uL) was added to the CHP nanogel solution using a micropipette. After the addition, ultrasonic waves were applied for 5 minutes, then 8.8 uL of 10×PBS was added, and ultrasonic irradiation was continued for another 5 minutes. The obtained solution was used as a Chol-CpG (D35)/CHP nanogel complex sample for further analysis.

Test Example 2-4. HPLC Analysis of Complex

As the complexation evaluation of the Chol-CpG (D35)/CHP nanogel complex sample prepared in Test Example 2-3, size exclusion chromatography (SEC) was carried out in the same manner as in Test Example 1-6.

Figure 5:
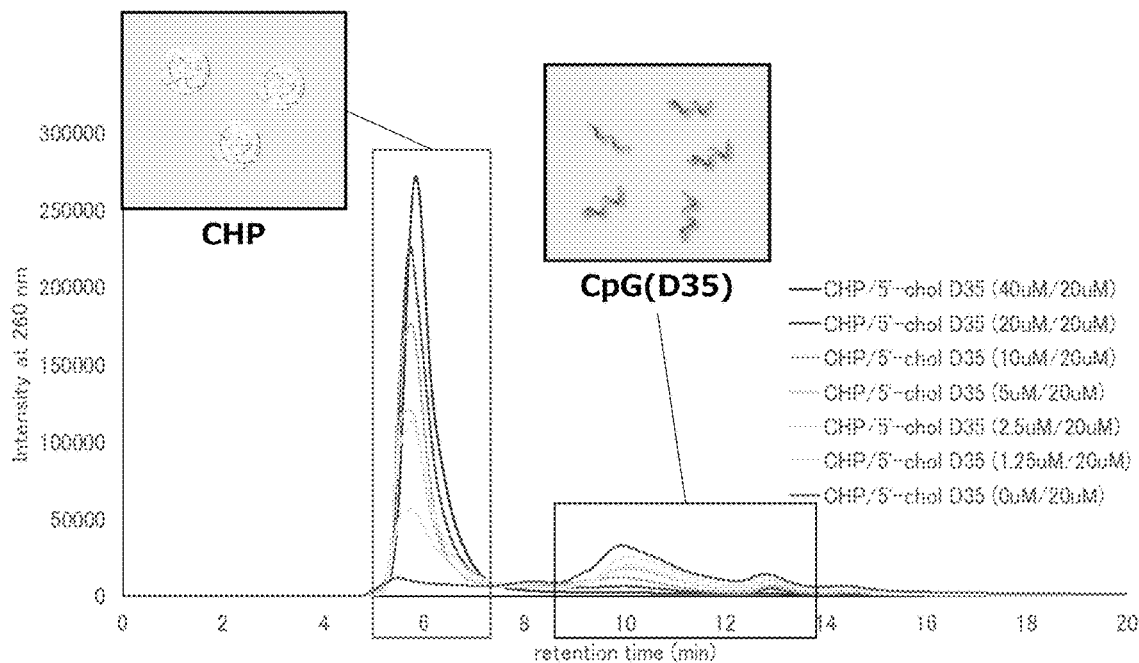
FIG. 5 shows the chromatograms of HPLC analysis results in Test Example 2-4.

The chromatograms are shown in FIG. 5. In the chromatogram of Chol-CpG (D35) (20 uM) alone (green line), several broad peaks derived from Chol-CpG (D35) were detected at around 8 to 15 minutes. Chol-CpG (K3) showed a sharp single peak at around 10 minutes, whereas Chol-CpG (D35) showed several broad peaks, suggesting that Chol-CpG (D35) formed multi-species aggregates in PBS. On the other hand, it was confirmed that as the molar ratio of the nanogel increased from 1.25:20 to 40:20 during complexation of CHP nanogel and Chol-CpG (D35) (light green line to dark blue line), the intensity of a sharp single peak derived from the complex at around 6 minutes increased, and the intensity of the peaks derived from Chol-CpG (D35) at around 8 to 15 minutes decreased. The increase of the large single peak at around 6 minutes in the complex sample indicates that the nanogel and Chol-CpG (D35) formed a complex. This can also be confirmed by the significant decrease in the Chol-CpG (D35) peak, which should have been detected at around 8 to 15 minutes.

Figure 6:
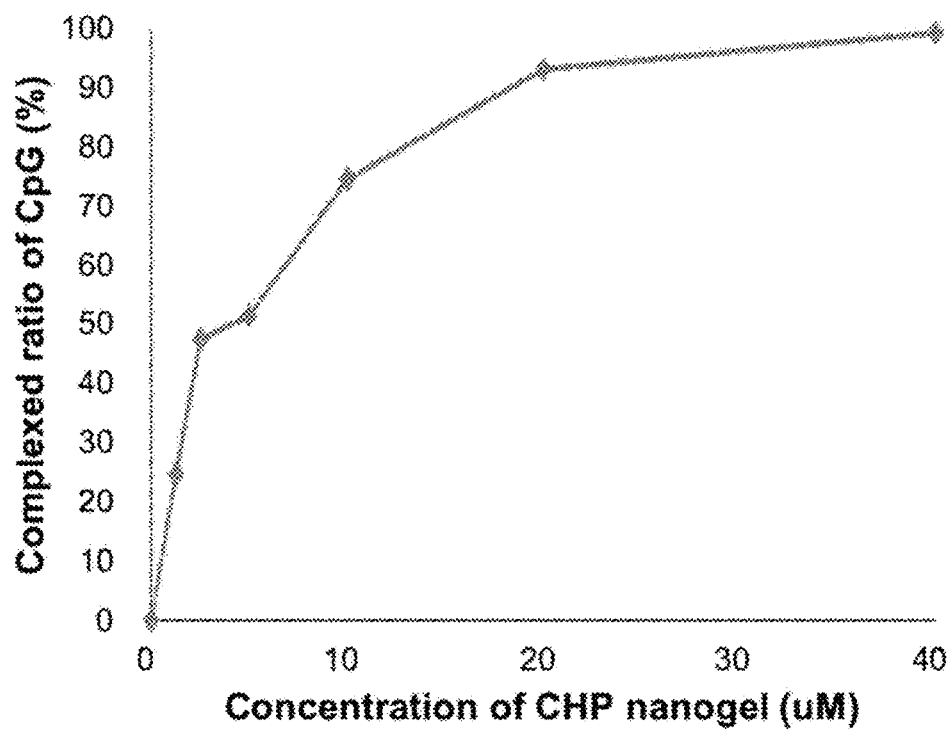
FIG. 6 shows the complexed ratio of the HPLC analysis results in Test Example 2-4.

The complexed ratio is shown in FIG. 6. The area of the peaks derived from Chol-CpG (D35) that was not complexed with the nanogel at around 8 to 15 minutes was analyzed, and the complexed ratio with the nanogel was graphed. As the CHP nanogel concentration during complexation increased, the peaks derived from the non-complexed Chol-CpG (D35) decreased. The complexed ratio was almost 100% at a molar ratio of nanogel with a CHP nanogel concentration of 40 uM and Chol-CpG (D35) of 2:1, and the complexed ratio was about 90% at a molar ratio of 1:1.

Test Example 2-5. Evaluation of Physical Properties of Complex (DLS)

For the complex (final concentration: 9 uM) prepared in Test Example 2-4 with Chol-CpG (D35): 10 uM and CHF nanogel: 10 uM, the particle diameter was measured using a dynamic light scattering (DLS) instrument in the same manner as in Test Example 1-7. The results are shown in Table 2.

TABLE 2

| | $D_H$ (nm) | PDI |
|---|---|---|
| CHP | 32.6 ± 5.9 | 0.24 ± 0.02 |
| Chol-CpG(D35)/CHP nanogel (9 uM/9 uM) | 28.1 | 0.21 |

The results were about 33 nm in CHP nanogel alone and about 28 nm in the complex sample. The particle diameter of the complex sample was similar to that of CHP nanogel alone. No significant increase in particle diameter due to aggregate formation was detected.

Test Example 3. Interaction Between CpG/CHP Nanogel Complex and Cells

In order to investigate the interaction between a CHP nanogel/Chol-CpG complex and cells, the complex was prepared using rhodamine-modified CHP (CHP—Rh) and Chol-CpG (5'-chol, 3'-FAM CpG) modified with fluorescein at the 3'-end, and the interaction with mouse macrophage-like cells (RAW 264.7) was evaluated using a confocal laser scanning microscope and flow cytometry.

Test Example 3-1. Preparation of CHP—Rh Nanogel/5'-Chol, 3'-FAM CpG Complex

Under ultrasonic irradiation (28 kHz, 100 W), 10 uL of 5'-chol, 3'-FAM CpG (K3 and D35)/water (200 uM) heated at 90° C. for 5 minutes was added to 90 uL of CHP—Rh nanogel/water (10 mg/mL), and ultrasonic irradiation was continued for 5 minutes. Thereafter, 10×PBS was added while applying ultrasonic waves, and ultrasonic irradiation was performed for another 5 minutes to prepare a complex using 1×PBS as a solvent.

Test Example 3-2. Observation with Confocal Laser Scanning Microscope 190 uL of RAW 264.7 suspension (medium: DMEM+10% FBS) was seeded at $5.0 \times 10^5$ cells/mL in a glass bottom dish, and pre-cultured overnight. After culture, 10 uL of a CHP—Rh nanogel/5'-chol, 3'-FAN CpG (K3 and D35) complex solution was added (nanogel and CpG final concentration: 1 uM), and allowed to stand in a $CO_2$ incubator at 37° C. for 4 hours. After standing still, the medium was removed, and the cells were washed with PBS and then observed using a confocal laser scanning microscope (LSM510 META, produced by Zeiss).

Figure 7:
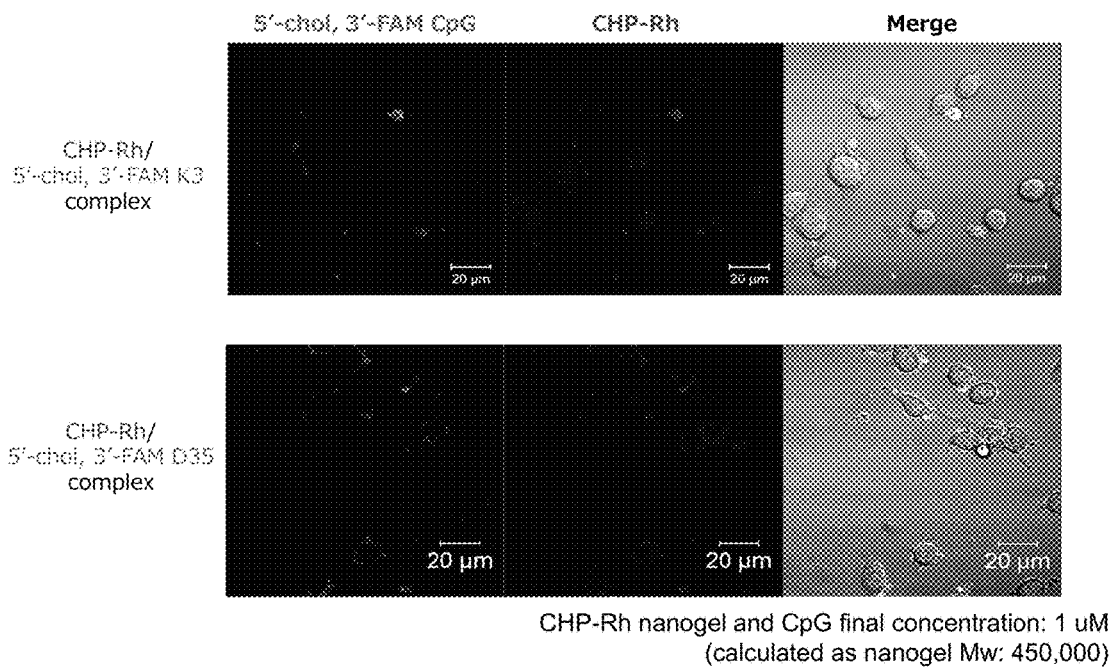
FIG. 7 shows confocal laser scanning micrographs in Test Example 3-2.

The results are shown in FIG. 7. In both complexes, fluorescence derived from the Rh of the nanogel (red) and the FAM of Chol-CpG (green) was observed in the cells, and it was confirmed that the nanogel and Chol-CpG were incorporated into the RAW 264.7 cells. Further, the subcellular localization of Rh and FAN fluorescence was also observed to be consistent in many areas, suggesting that the nanogel and Chol-CpG were incorporated into the cells simultaneously, i.e., in a complex form.

Test Example 3-3. Evaluation by Flow Cytometry 450 uL of RAW 264.7 suspension (medium: DMEM+10% FBS) was seeded at $1.0 \times 10^6$ cells/mL in a 12-well plate, and pre-cultured overnight. After culture, 50 uL of a CHP—Rh nanogel/5'-chol, 3'-FAM CpG (K3 and D35) complex solution was added (final concentration: 1 uM for each), and allowed to stand in a $CO_2$ incubator at 37° C. for 4 hours. After standing still, the medium was removed, and the cells were washed with PBS. Then, the cells were isolated by collagenase to prepare a cell suspension, which was then analyzed by flow cytometry.

Figure 8:
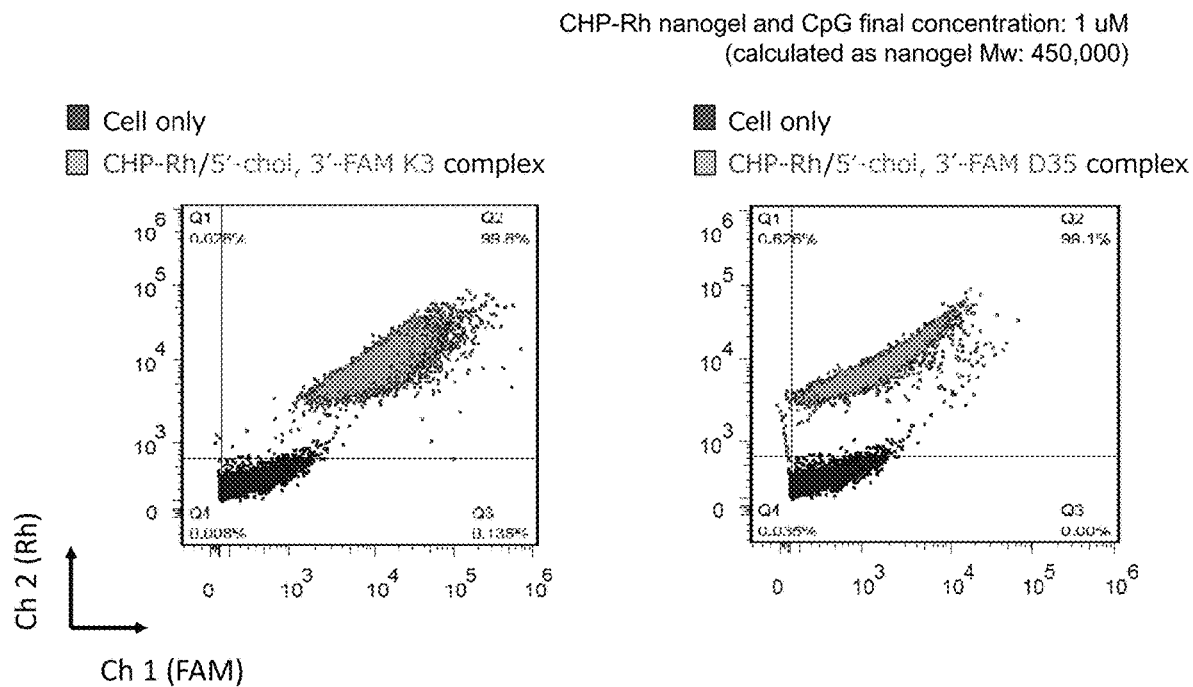
FIG. 8 shows the scattergrams of flow cytometry analysis in Test Example 3-3.

The results are shown in FIG. 8. In the cells to which the CHP—Rh nanogel/5'-chol, 3'-FAN CpG complex was added, both the FAM fluorescence intensity of Ch1 and the Rh fluorescence intensity of Ch2 were increased. In the CHP—Rh nanogel/5'-chol, 3'-FAM CpG (K3) complex, almost all of the cells were in the double positive region, and it was confirmed that almost all of the cells incorporated the nanogel and Chol-CpG (K3). Further, in the CHP—Rh nanogel/5'-chol, 3'-FAM CpG (035) complex, 50% or more of the cells were detected in the double positive region, indicating that the CHP nanogel/Chol-CpG complex could be incorporated into the cells at a high frequency.

Test Example 4. CpG Activity Evaluation 1

180 uL of RAW 264.7 suspension (medium: DMEM+ 10% FBS) was seeded at $2.5 \times 10^5$ cells/mL in a 96-well plate, and pre-cultured overnight. After culture, 20 uL of each sample (Table 3) was added to each well to a concentration shown in Table 3, mixed, and cultured in a $CO_2$ incubator for 2 days. cGAMP, which is known as a STING receptor agonist, was included in the samples as a positive control. After culture, the culture supernatant in each well was collected, and diluted 5 times with a blocking buffer to provide an ELISA sample. The TNF-alpha concentration of the culture supernatant was measured according to the protocol of Mouse TNF-alpha ELISA kit (produced by Invitrogen).

TABLE 3

| | cGAMP | CpG(K3) | Chol-CpG(K3) | CHP nanogel/Chol-CpG (K3) complex |
|---|---|---|---|---|
| Final concentration | 15 uM | 2 uM | 2 uM | 2 uM |

Figure 9:
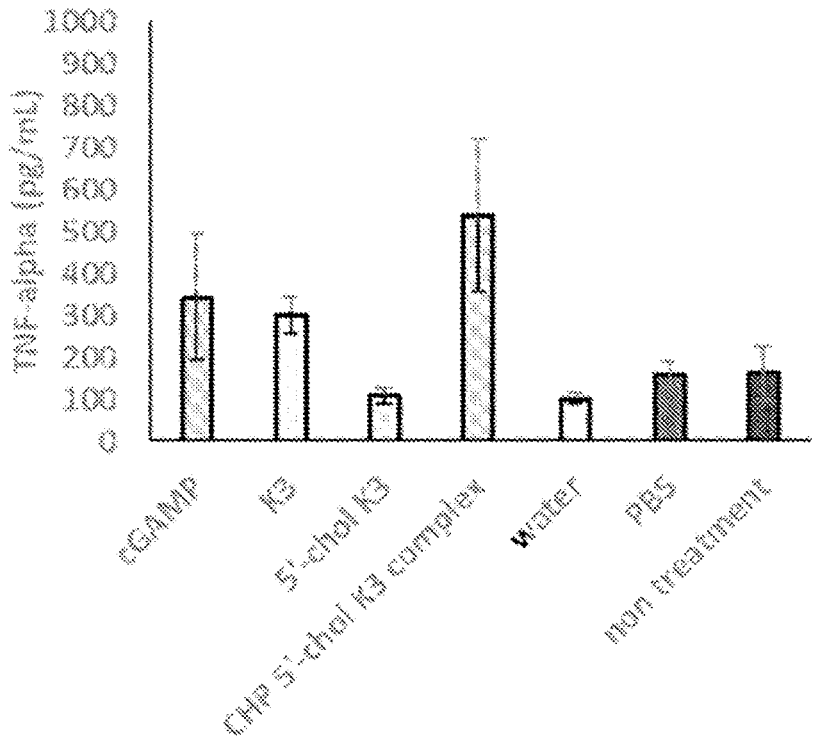
FIG. 9 shows the ELISA results of Test Example 4.

The results are shown in FIG. 9. When the CHP nanogel/Chol-CpG (K3) complex was added, the TNF-alpha concentration increased, and this concentration was higher than that when the same concentration of CpG (K3) and Chol-CpG (K3) was added. The results suggested that the CHP nanogel/Choi-CpG (K3) complex could induce cytokine production equal to or higher than when CpG (K3) was added alone.

Test Example 5. Evaluation of Therapeutic Effects

Mouse lymphoma E.G7-OVA cells were cultured in RPMI 1640 medium (10% FBS, 1% penicillin-streptomycin, 400 μg/mL G418, 2 mM mercaptoethanol). The cells were diluted with PBS, and $1.0 \times 10^6$ cells were subcutaneously transplanted into normal mice (C57BL/6, 6-week-old, females). 8, 10, and 13 days after transplantation, 20 μg as DNA of the CHP nanogel/Chol-CpG (K3) complex was intravenously administered. 8, 10, 13, 15, 17, 20, and 22 days after transplantation, 200 μg of anti-PD-1 antibody (clone RMP1-14, Bio X Cell) was intraperitoneally administered. An equal volume of PBS was administered to each of the mice in the negative control group. Each group included 4 or 5 individuals. From 8 days after transplantation, the long and short diameters of the tumor were measured, and the tumor volume was calculated by the equation (tumor volume=long diameter×(short diameter)$^2$/2). Each numerical value indicates mean±standard deviation. For the tumor volume on day 21 after transplantation, significant differences between the groups were determined by the Mann-Whitney U test.

Figure 10:
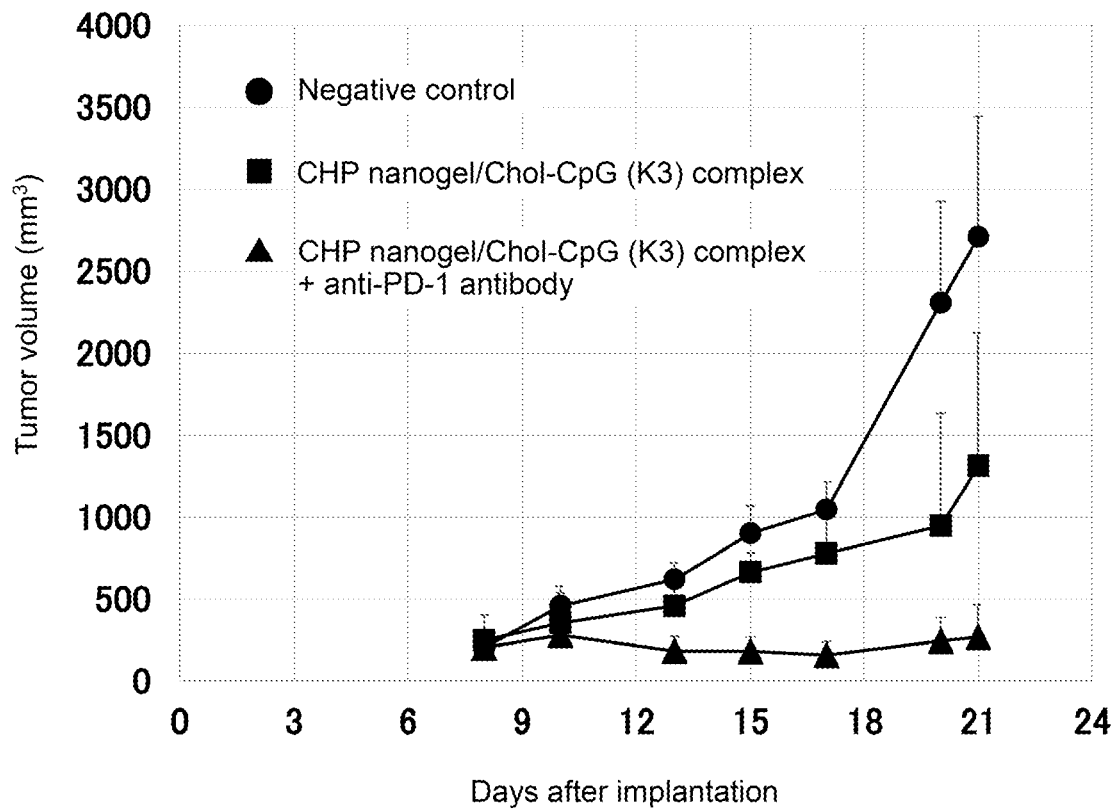
FIG. 10 shows the results of measuring the tumor volume in Test Example 5.

The results are shown in FIG. 10. In the figure, * denotes $p<0.1$, and ** denotes $p<0.02$. A decrease in tumor volume was observed after the administration of the CHP nanogel/Choi-CpG (K3) complex. It was also revealed that the combined use with the anti-PD-1 antibody could enhance the anticancer effects.

Test Example 6. Biodistribution Analysis

Mouse lymphoma E.G7-OVA cells were cultured in RPMI 1640 medium (10% FBS, 1% penicillin-streptomycin, 400 μg/mL G418, 2 mM mercaptoethanol). The cells were suspended in PBS, and $1.0 \times 10^6$ cells were subcutaneously transplanted into normal mice (C57BL/6, 6-week-old, females). 5 days after transplantation, 7 μg as DNA of the CHP nanogel/Chol-CpG (K3) complex or Chol-CpG (K3) was intravenously administered. These included fluorochrome (FAM)-labeled Chol-CpG (K3). PBS was administered as a negative control. 6 hours after administration, blood was collected under anesthesia, and various organs (heart, lung, liver, spleen, kidney, and cancer tissue) were removed. The removed organs were each placed on a 24-well culture plate and fluorescence-photographed using IVIS. Further, the wet weight of each organ was measured. The average fluorescence intensity detected in each organ was standardized by the organ weight and graphed.

Figure 11:
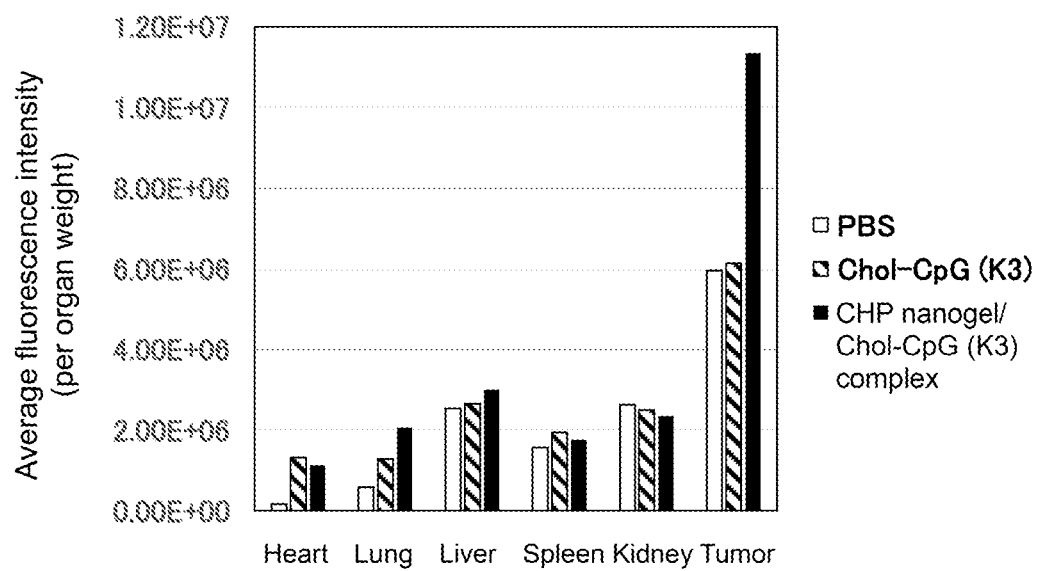
FIG. 11 shows the results of measuring the amount of Chol-CpG (K3) in each tissue in Test Example 6.

The results are shown in FIG. 11. It was revealed that complexes of Chol-CpG (K3) and CHP nanogel could be selectively delivered to main tissues.

Test Example 7. CpG Activity Evaluation 2

Mice (C57BL/6j, females, 8-week-old) were euthanized, and the spleen was collected, suspended in RMPI medium (10% FBS) to $1 \times 10^6$ cells/well, and seeded in a 96-well plate. After incubation for 3 hours, CpG (K3) ("K3 Free" in the figure) or the CHP nanogel/Chol-CpG (K3) complex ("K3 complex" in the figure) was added at a concentration of 1 μM, and incubated for 24 hours, and the supernatant was collected. 100 ng/mL LPS was added as a positive control, and PBS was added as a negative control. The supernatant was centrifuged (2000×g, 4° C., 10 minutes), and the resulting supernatant was collected. The collected culture supernatant was diluted 3 to 5 times with a diluent included in an ELISA kit, and the resultant was used as an ELISA sample. These were measured according to the protocols of TNF-alpha ELISA kit (Invitrogen), Mouse IL-12p70 ELISA DuoSet (R&D Systems), and Mouse IL-6 ELISA DuoSet (R&D Systems). Each numerical value indicates the mean concentration±standard deviation of each cytokine in the culture supernatant. Significant differences between the groups were determined by the Student's t test.

Figure 12:
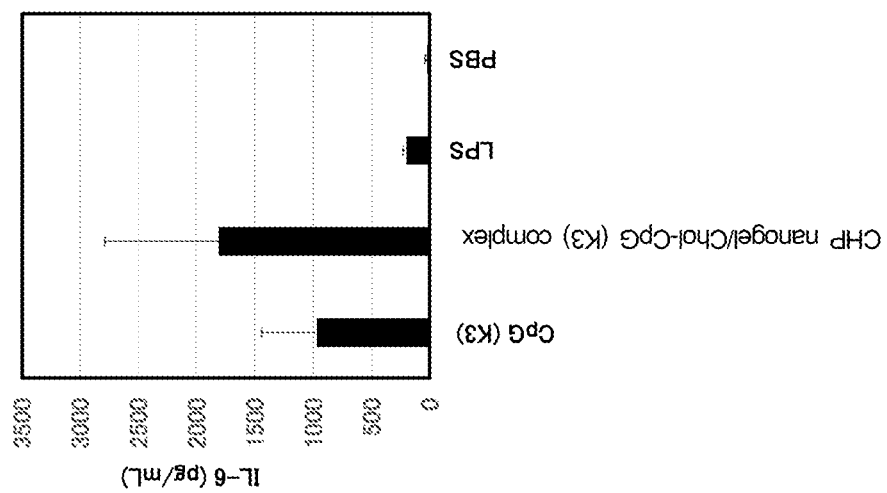
FIG. 12 shows the ELISA results of Test Example 7.
Figure 12:
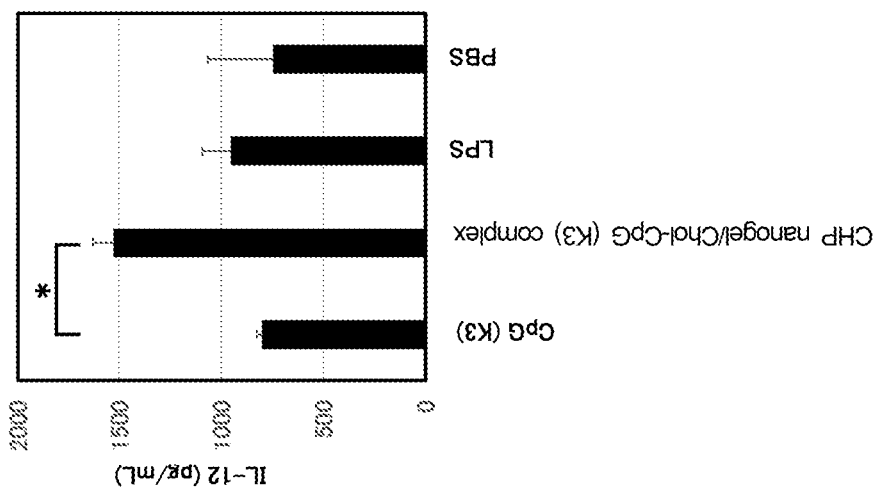
Figure 12:
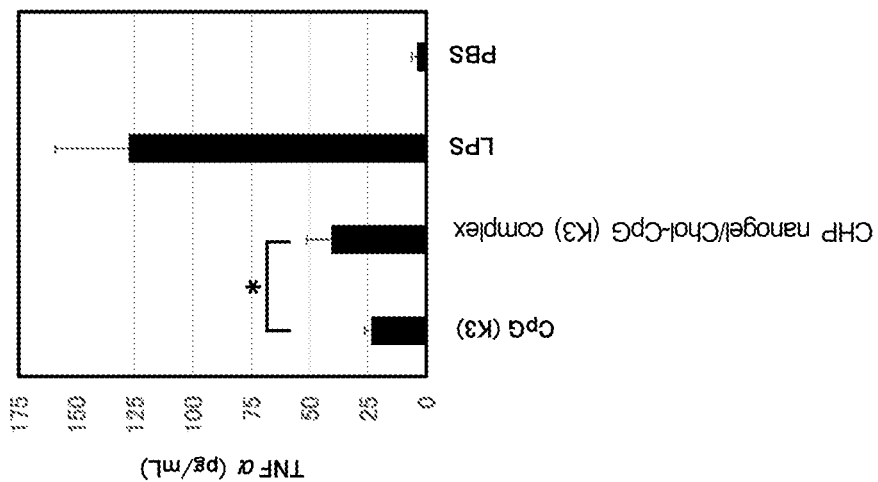

The results are shown in FIG. 12. In the figure, * denotes $p<0.05$. It was suggested that the CHP nanogel/Chol-CpG (K3) complex could induce cytokine production equal to or higher than when CpG (K3) was added alone.

The invention claimed is:

1. A complex comprising a modified CpG oligonucleotide containing a hydrophobic group A having a sterol skeleton, and a modified polysaccharide containing a hydrophobic group B, wherein the polysaccharide that forms the modified polysaccharide comprises pullulan, and the hydrophobic group B comprises a hydrophobic group having a sterol skeleton.

2. The complex according to claim 1, wherein a CpG oligonucleotide that forms the modified CpG oligonucleotide comprises at least one member selected from the group consisting of class A CpG oligonucleotides and class B CpG oligonucleotides.

3. The complex according to claim 1, wherein the hydrophobic group A comprises at least one member selected from the group consisting of cholesterol-derived groups, cholestanol-derived groups, lanosterol-derived groups, ergosterol-derived groups, β-sitosterol-derived groups, campesterol-derived groups, stigmasterol-derived groups, and brassicasterol-derived groups.

4. The complex according to claim 1, wherein the number of nucleotides that form the modified CpG oligonucleotide is 8 to 50.

5. The complex according to claim 1, wherein the modified polysaccharide has a weight average molecular weight of 5000 to 2,000,000.

6. The complex according to claim 1, which contains 0.1 to 10 molar parts of the modified polysaccharide per molar part of the modified CpG oligonucleotide.

7. The complex according to claim 1, which is nanogel particles.

8. A reagent comprising the complex according to claim 1.

9. A drug comprising the complex according to claim 1.

10. The drug according to claim 9, which is an immunomodulator, an anticancer agent, an adjuvant, or an antiviral agent.

* * * * *